(12) United States Patent
Park et al.

(10) Patent No.: US 11,590,047 B2
(45) Date of Patent: Feb. 28, 2023

(54) WALKING ASSISTANCE APPARATUS

(71) Applicant: Samsung Electronics Co., Ltd., Suwon-si (KR)

(72) Inventors: Youngjin Park, Seoul (KR); Hyun Do Choi, Yongin-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 133 days.

(21) Appl. No.: 16/427,471

(22) Filed: May 31, 2019

(65) Prior Publication Data

US 2020/0113771 A1    Apr. 16, 2020

(30) Foreign Application Priority Data

Oct. 12, 2018   (KR) .......................... 10-2018-0121999

(51) Int. Cl.
| | |
|---|---|
| *A61H 3/00* | (2006.01) |
| *A63B 21/00* | (2006.01) |
| *A61F 5/01* | (2006.01) |
| *B25J 9/00* | (2006.01) |

(52) U.S. Cl.
CPC .............. *A61H 3/00* (2013.01); *A61F 5/0127* (2013.01); *A63B 21/4011* (2015.10); *B25J 9/0006* (2013.01)

(58) Field of Classification Search
CPC ................................................... A61F 5/0127
See application file for complete search history.

(56) References Cited

U.S. PATENT DOCUMENTS

| | | | | |
|---|---|---|---|---|
| 2,206,234 | A | | 7/1940 | Murray |
| 3,805,773 | A | * | 4/1974 | Sichau .................. A61F 5/0127 602/28 |
| 4,573,457 | A | * | 3/1986 | Parks .................... A61F 5/0127 36/102 |
| 4,955,370 | A | * | 9/1990 | Pettine .................. A61F 5/0127 602/28 |
| 5,086,760 | A | * | 2/1992 | Neumann ............. A61F 5/0123 602/16 |
| 5,215,508 | A | * | 6/1993 | Bastow .................. A63B 23/08 482/79 |

(Continued)

FOREIGN PATENT DOCUMENTS

| | | |
|---|---|---|
| CN | 108338896 A | 7/2018 |
| JP | 2004-261622 | 9/2004 |

(Continued)

OTHER PUBLICATIONS

Luke M. Mooney et al., "Autonomous exoskeleton reduces metabolic cost of human walking during load carriage", Journal of Neuroengineering and Rehabilitation, 11, 1-6, 2014.

(Continued)

*Primary Examiner* — Jacqueline Woznicki
(74) *Attorney, Agent, or Firm* — Harness, Dickey & Pierce, P.L.C.

(57) ABSTRACT

A walking assistance apparatus includes a frame configured to be mounted on a lower leg of a user, a sole support connected to the frame and configured to support a lower side of a foot of the user, an actuator mounted on the frame, and a pusher configured to receive a power from the actuator and push the ground.

15 Claims, 14 Drawing Sheets

(56) References Cited

U.S. PATENT DOCUMENTS

| | | | | |
|---|---|---|---|---|
| 6,056,712 | A * | 5/2000 | Grim | A61F 5/0127 602/16 |
| 6,171,272 | B1 * | 1/2001 | Akita | A61F 5/0127 602/27 |
| 6,464,659 | B1 * | 10/2002 | DeToro | A61F 5/0195 602/23 |
| 9,492,302 | B2 | 11/2016 | Wiggin et al. | |
| 2005/0038365 | A1 * | 2/2005 | Scott | A61F 5/0113 602/23 |
| 2005/0070834 | A1 * | 3/2005 | Herr | A61H 3/00 602/28 |
| 2007/0244420 | A1 * | 10/2007 | Boden | A61F 5/0127 602/27 |
| 2011/0021963 | A1 * | 1/2011 | Graddon | A61F 5/0127 602/27 |
| 2011/0196277 | A1 * | 8/2011 | Savard | A61F 5/0127 602/28 |
| 2012/0259429 | A1 | 10/2012 | Han et al. | |
| 2013/0000156 | A1 * | 1/2013 | Andoh | A43B 3/0005 36/136 |
| 2014/0088728 | A1 * | 3/2014 | Herr | A61F 2/64 623/32 |
| 2015/0209214 | A1 | 7/2015 | Herr et al. | |
| 2016/0250094 | A1 * | 9/2016 | Amundson | A61H 1/0266 623/24 |
| 2017/0172782 | A1 * | 6/2017 | McDonnell, Jr. | A61F 5/0127 |
| 2017/0202724 | A1 * | 7/2017 | De Rossi | A61F 5/0102 |
| 2018/0092795 | A1 | 4/2018 | Fagan | |
| 2018/0125681 | A1 * | 5/2018 | Seifert | A61F 2/64 |
| 2018/0125738 | A1 | 5/2018 | Witte et al. | |
| 2018/0177664 | A1 | 6/2018 | Choi et al. | |
| 2018/0228684 | A1 * | 8/2018 | Park | B25J 9/0006 |
| 2018/0256435 | A1 | 9/2018 | Zhang et al. | |
| 2019/0015284 | A1 * | 1/2019 | Horst | A61H 1/024 |
| 2019/0298564 | A1 * | 10/2019 | Van Der Wilk | A61F 5/0111 |
| 2021/0052458 | A1 * | 2/2021 | Gutierrez Gonzalez | A61F 5/0123 |

FOREIGN PATENT DOCUMENTS

| | | |
|---|---|---|
| JP | 2014-068868 A | 4/2014 |
| JP | 2016-101227 A | 6/2016 |
| JP | 6253049 B2 | 12/2017 |
| JP | 2018-075262 | 5/2018 |
| KR | 10-1025512 B1 | 4/2011 |
| KR | 10-1187018 B1 | 9/2012 |
| KR | 10-1363834 | 2/2014 |
| KR | 10-1430867 B1 | 8/2014 |
| WO | WO-2018/098849 A1 | 6/2018 |

OTHER PUBLICATIONS

Gregory S. Sawicki et al., "Mechanics and energetics of level walking with powered ankle exoskeletons", The Journal of Experimental Biology, The Company of Biologists, vol. 211, p. 1402-1413, 2008.

"CoCoroe AAD(Ankle-Assist Device)", Yasakawa Electric Corporation, http://www.e-mechatronics.com/cocoroe/aad/#function, retrieved via the internet.

Extended European Search Report (EESR) issued by European Patent Office dated Nov. 27, 2019 for EP Patent Application No. 19193662.4.

Office Action issued by Korean Intellectual Property Office (KIPO) dated Dec. 29, 2022 for the corresponding KR Patent Application No. 10-2018-0121999.

* cited by examiner

WALKING ASSISTANCE APPARATUS

CROSS-REFERENCE TO RELATED APPLICATION

This application claims under 35 U.S.C. § 119 to Korean Patent Application No. 10-2018-0121999, filed on Oct. 12, 2018, in the Korean Intellectual Property Office, the entire contents of which are incorporated herein by reference in its entirety.

BACKGROUND

1. Field

At least one example embodiment relates to a walking assistance apparatus.

2. Description of the Related Art

Walking assistance apparatuses enabling the elderly and/or patients having joint problems to walk with less effort, and apparatuses for assisting muscular strength of users, for example, for military purposes are being developed.

SUMMARY

Some example embodiments relate to a walking assistance apparatus.

In some example embodiments, the walking assistance apparatus may include a frame configured to mount on a lower leg of a user; a sole support connected to the frame, the sole support configured to support a sole of a foot of the user; a pusher configured to move relative to the frame to push a ground in response to power transferred thereto; and an actuator on the frame, the actuator configured to transfer the power to the pusher.

In some example embodiments, the pusher is indirectly connected to the sole support.

In some example embodiments, the sole support is configured to lift the sole of the foot while the pusher is pushing the ground.

In some example embodiments, the pusher is configured to spaced apart from the foot.

In some example embodiments, the actuator comprises a first rod movable with respect to the frame, the first rod configured to support a first portion of the pusher; and a second rod movable with respect to the frame at a higher speed than that of the first rod, the second rod configured to support a second portion of the pusher.

In some example embodiments, the first rod is configured to perform a translational motion with respect to the frame, and the second rod is configured to perform the translational motion and a rotational motion with respect to the frame.

In some example embodiments, the walking assistance apparatus further includes a toe support connected to the pusher such that the toe support extends towards the foot of the user from the pusher when the user wears the walking assistance apparatus, the toe support configured to support a toe of the user.

In some example embodiments, a material of the toe support is more flexible than a material of the pusher.

In some example embodiments, the walking assistance apparatus further includes a cover connected to the pusher such that the cover extends towards the foot of the user from the pusher when the user wears the walking assistance apparatus, the cover configured to cover a portion of a side of the foot of the user.

In some example embodiments, the pusher is configured to perform a translational motion in one degree of freedom (DOF) with respect to the frame.

In some example embodiments, the pusher comprises: a first pusher part connected to the actuator, the first pusher part configured to receive the power from the actuator; and a second pusher part connected to the first pusher part at an angle with respect to the first pusher part, the second pusher part configured to contact the ground when the user wears the walking assistance apparatus.

In some example embodiments, the pusher is configured to perform a rotational motion in one DOF with respect to the frame.

In some example embodiments, the sole support includes a first end and a second end, the first end and the second end each being connected to the frame such that the sole support is configured to enclose a heel of the user when the user wears the walking assistance apparatus.

In some example embodiments, a length of the pusher is adjustable.

In some example embodiments, the frame includes a frame body configured to mount on the lower leg; and a frame extension portion extending from the frame body towards the user to cover at least a portion of the lower leg of the user, the frame extension portion configured to support the sole support.

Some example embodiments relate to a walking assistance apparatus.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
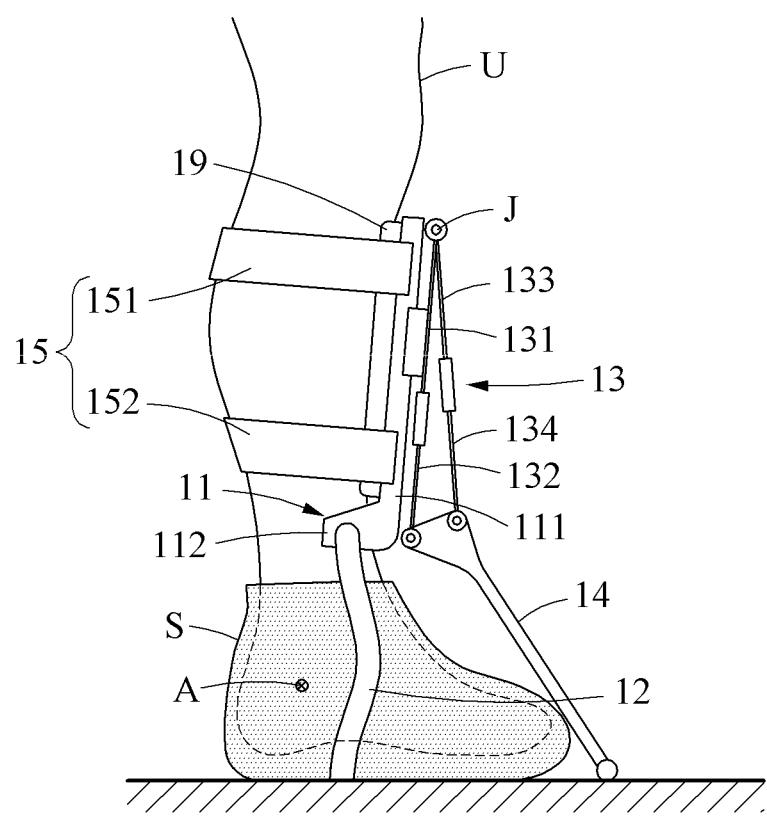
FIG. 1 is a side view illustrating an example of a walking assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Figure 2:
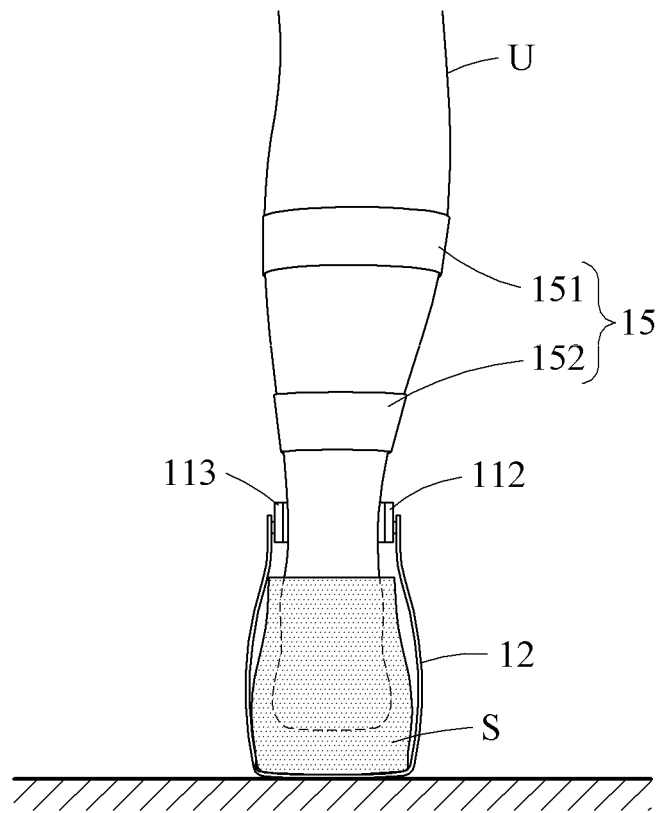
FIG. 2 is a rear view illustrating a walking assistance apparatus according to at least one example embodiment.
Figure 3:
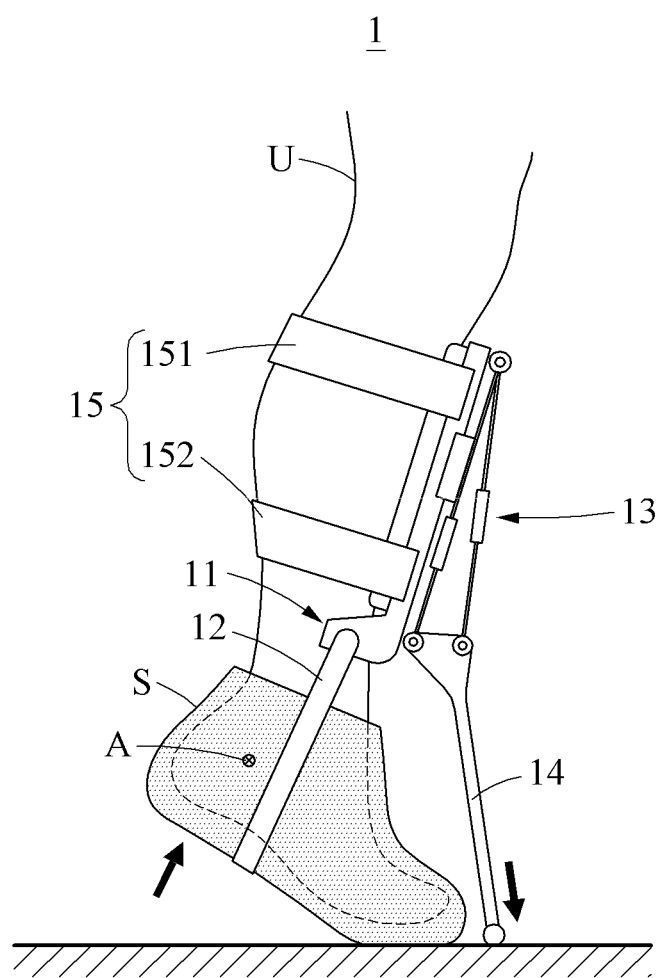
FIG. 3 illustrates an example in which a walking assistance apparatus according to at least one example embodiment assists a push-off motion.
Figure 4:
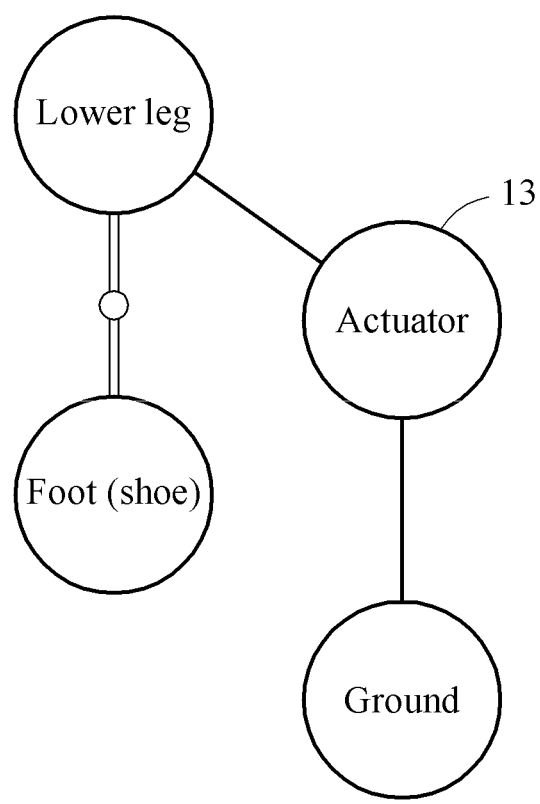
FIG. 4 is a block diagram illustrating an actuator of a walking assistance apparatus that interacts with a shin and the ground according to at least one example embodiment.

FIG. 1 is a side view illustrating an example of a walking assistance apparatus according to at least one example embodiment, and FIG. 2 is a rear view illustrating a walking assistance apparatus according to at least one example embodiment. FIG. 3 illustrates an example in which a walking assistance apparatus according to at least one example embodiment assists a push-off motion. FIG. 4 is a block diagram illustrating an actuator of a walking assistance apparatus that interacts with a shin and the ground according to at least one example embodiment.

Referring to FIGS. 1 through 4, a walking assistance apparatus 1 may be worn by a user to assist walking of the user. The user may be, for example, a human, an animal, or a robot.

The walking assistance apparatus 1 may assist a push-off motion of the user. In the push-off motion, a stance leg of the user is almost stretched, and a motion of stretching an ankle has an effect of pushing the center of gravity of the user forward. The walking assistance apparatus 1 may apply a torque for stretching the ankle by interacting with the ground and a lower leg. The walking assistance apparatus 1 may assist walking of the user by applying the torque for stretching the ankle.

The walking assistance apparatus 1 may not directly apply a force to an ankle joint to assist the walking of the user. Instead, the walking assistance apparatus 1 may assist walking by lifting a heel instead of bending or stretching an ankle joint. Since the walking assistance apparatus 1 does not apply a force and/or torque directly to the ankle joint, a center of driving may not need to be accurately aligned with the ankle joint. Despite a misalignment between the ankle joint and the center of driving, the walking assistance apparatus 1 may efficiently assist walking by minimizing a force to be wasted.

The walking assistance apparatus 1 may apply a force onto the ground, and may assist walking using a reaction force against the force. The walking assistance apparatus 1 may include a frame 11, a sole support 12, an actuator 13, a pusher 14 (or, alternatively, a crutch), a wearable band 15, and a cushion 19.

The pusher 14 may be moved toward the ground by the actuator 13 to push the ground. Due to a reaction against a force applied to the ground by the pusher 14, the sole support 12 may move upward to lift a heel of a user.

The walking assistance apparatus 1 may have an available space around an ankle joint of a user instead of firmly fixing the ankle joint, to enhance a user wearability.

The frame 11 may be disposed on a lower leg. For example, the frame 11 may be mounted on a front side of the lower leg, that is, a shin, or mounted on a side of the lower leg, however, example embodiments are not limited thereto. For example, the frame 11 may be mounted on a rear side of the lower leg, that is, a calf. The frame 11 may support the actuator 13.

The frame 11 may include a frame body 111, a first frame extension portion 112 and a second frame extension portion 113.

The frame body 111 may be mounted on a lower leg of a user. The frame body 111 may have an elongated shape in a longitudinal direction of the lower leg. The frame body 111 may have a shape corresponding to a shape of the lower leg, and may cover at least a portion of the lower leg. An inner surface of the frame body 111 may face the user, and the actuator 13 may be disposed on an outer surface of the frame body 111.

The first frame extension portion 112 and the second frame extension portion 113 may extend to cover the lower leg from the frame body 111. For example, when the frame body 111 is mounted on the front side of the lower leg, the first frame extension portion 112 and the second frame extension portion 113 may be formed to extend backward from the frame body 111. The first frame extension portion 112 may extend backward from one side of the frame body 111, and the second frame extension portion 113 may extend backward from another side of the frame body 111. The first frame extension portion 112 and the second frame extension portion 113 may face each other, and may cover at least a portion of the lower leg together with the frame body 111. The first frame extension portion 112 and the second frame extension portion 113 may support both end portions of the sole support 12. The first frame extension portion 112 and the second frame extension portion 113 may perform an assistance in a state in which the frame body 111 is disposed on the shin so that the sole support 12 may stably support a bottom, for example, a heel, of a foot. Due to the first frame extension portion 112 and the second frame extension portion 113, the sole support 12 may be formed to have a relatively short length. Also, a portion of the frame 11 supporting the sole support 12 may be designed to extend backward, and thus a size of the frame 11 and a weight of the walking assistance apparatus 1 may be reduced.

The sole support 12 may be connected to the frame 11, and may support a foot, for example, a heel, of a user. When the actuator 13 allows the pusher 14 to push the ground in a push-off motion, the frame 11 may be lifted, and accordingly the sole support 12 may also be lifted so that the heel may be lifted from the ground.

One end of the sole support 12 may be connected to the first frame extension portion 112, and another end of the sole support 12 may be connected to the second frame extension portion 113. For example, the sole support 12 may be a strap formed of a flexible material, for example, fabric, that has a relatively low elasticity or does not have an elasticity. In this example, due to a change in an elasticity of the sole support 12, a waste of a force transferred from the sole support 12 to the foot may be reduced (or, alternatively, prevented). Also, a temporal delay between a point in time at which the pusher 14 pushes the ground and a point in time at which the sole support 12 lifts the foot may be reduced, and thus it is possible to accurately and easily control a walking assistance. In another example, the sole support 12 may include an elastic body with an elasticity.

Although the sole support 12 has a band shape to enclose a foot, example embodiments are not limited thereto. The sole support 12 may have all shapes to support a sole. For example, the sole support 12 may have a shape of "L" that includes a first part extending downward from the frame 11 and a second part that extends in a direction intersecting the first part and that supports a sole of a user. For example, the first part may be a strap formed of a flexible material, for example, fabric, that has a relatively low elasticity or does not have an elasticity, and the second part may be a plate formed of a rigid material, for example, plastic or metal.

The sole support 12 may have a length that is adjustable using various schemes, for example, a buckle or a snap button. The sole support 12 may easily enclose shoes with any shape. In the above structure, the length of the sole support 12 may be adjusted based on a toe-off state in which a plantar-flexion angle is maximized. In this example, the sole support 12 may be relatively loosened because a force is not applied in a dorsi-flexion motion, although the sole support 12 may be tightened because a force is applied in a push-off motion. In the above structure, the walking assistance apparatus 1 may assist walking so that a push-off operation may be performed while maintain a foot of a user at a natural angle.

Figure 7:
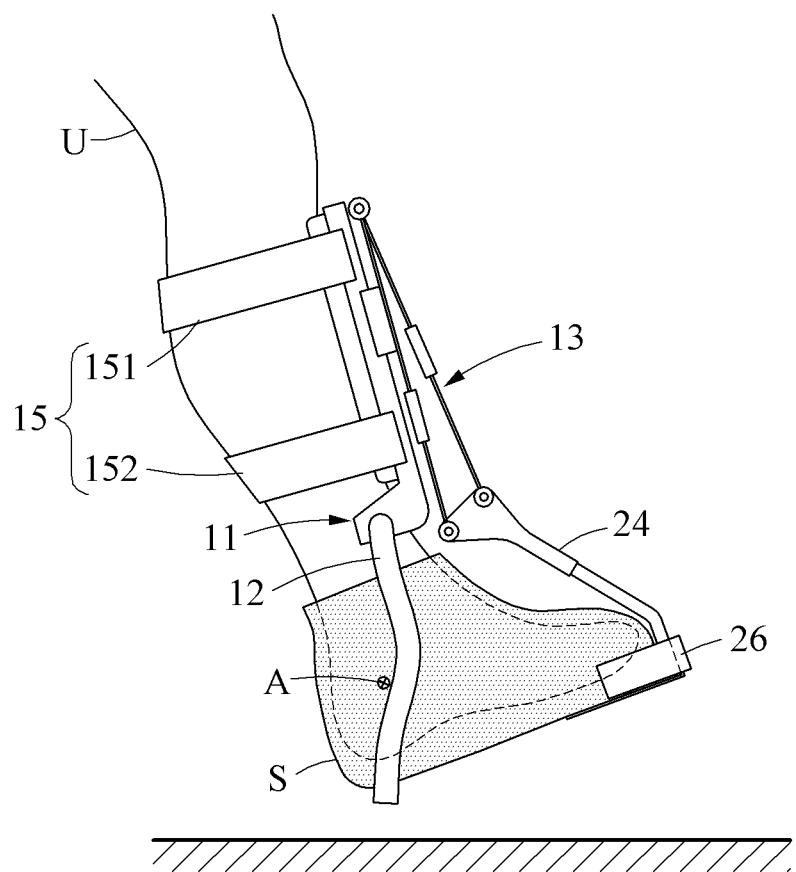
FIG. 7 illustrates an example in which a walking assistance apparatus according to at least one example embodiment supports toes in a swing phase.

The actuator 13 may generate a power to operate the pusher 14 using various schemes. For example, as shown in FIGS. 3 and 7, the actuator 13 may allow the pusher 14 to simultaneously perform a translation and a rotation. The actuator 13 may be disposed on the frame 11. The actuator 13 may include a first guide 131, a first rod 132, a second guide 133 and a second rod 134.

The actuator 13 may further include a drive source (not shown) that generates power to drive the actuator 13. For example, the drive source may be a motor. According to other example embodiments, the driving source 12 may include at least one piston or cylinder device that is operated by the electric energy or by fluidic pressure such as, for example, hydraulic pressure or pneumatic pressure. The drive source may be on the frame 11. Meanwhile, unlike the above, the drive source 71 may be on a portion spaced apart from the frame 11, and transmit the power to the actuator 13 through another power transmitting device such as a cable, a belt, or a gear train.

The actuator 13 may be connected to a controller (not shown), and the controller may be connected to one or more sensors (not shown) configured to sense various environmental factors such as pressure.

The controller may include a processor and a memory. The memory may include may include a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The processor may processor may be an arithmetic logic unit, a digital signal processor, a microcomputer, a field programmable array, a programmable logic unit, a microprocessor or any other device capable of responding to and executing instructions in a defined manner. The memory may contain computer readable code that, when executed by the processor, configures the processor as a special purpose computer.

For example, the memory may contain computer readable code that, when executed by the processor, configures the processor as a special purpose computer to determine a gait state based on data measured by the sensors, and instruct the actuator 13 to generate power to perform a plantar-flexion motion and to not generate the power during a dorsi-flexion motion such that, during the plantar-flexion motion, the walking assistance apparatus 1 may assist walking without applying a force and/or torque directly to the ankle joint of the user by instead applying a force to push the external pusher 14 against the ground.

The first guide 131 may be fixed to the frame 11. The first guide 131 may guide a movement direction of the first rod 132. The first rod 132 may perform a translation in one degree of freedom (DOF) with respect to the first guide 131. For example, the first rod 132 may slide along an inner wall or outer wall of the first guide 131. The first rod 132 may be connected to a first portion of the pusher 14.

The second guide 133 may be rotatably connected to the frame 11. For example, the second guide 133 may be rotatably connected to a joint J disposed on the frame 11. A relative angle between the second guide 133 and the first guide 131 may be changed. The second rod 134 may perform a translation in one DOF with respect to the second guide 133. For example, the second rod 134 may slide along an inner wall or outer wall of the second guide 133. The second rod 134 may be connected to a second portion of the pusher 14. The second portion of the pusher 14 may be farther away from the frame 11 than the first portion of the pusher 14.

The second rod 134 may perform a translation at a higher speed than that of the first rod 132. The first rod 132 and the second rod 134 may perform translations at different speeds, and accordingly the pusher 14 may simultaneously perform a translation and a rotation with respect to the frame body 111. For example, the pusher 14 may simultaneously perform a rotation about a remote center of motion (RCM) of the pusher 14. The RCM of the pusher 14 may be formed around an ankle joint of a user, however, example embodiments are not limited thereto. Although the RCM of the pusher 14 is not accurately aligned with the ankle joint, the pusher 14 may not apply a force and/or torque directly to the ankle joint so that walking of the user may be efficiently assisted.

The pusher 14 may push the ground. The pusher 14 may interact with the ground. The pusher 14 may receive a power from the actuator 13 to push the ground. For example, when the pusher 14 pushes the ground, the sole support 12 may lift a heel of a user due to a reaction thereof. The pusher 14 may be a longitudinal member. The pusher 14 may be in contact with a portion of the ground in front of the foot. The pusher 14 may be formed of a rigid material. The pusher 14 may not be deformed while pushing the ground.

The wearable band 15 may fix the frame 11 to a lower leg of a user. For example, the wearable band 15 may include a first wearable band 151 and a second wearable band 152 that are separated in a longitudinal direction of the lower leg. For example, the first wearable band 151 and the second wearable band 152 may be disposed on opposite sides of a thickest portion of a calf of a user. The first wearable band 151 may inhibit (or, alternatively, prevent) the frame 11 from being separated upward from the user, and the second wearable band 152 may inhibit (or, alternatively, prevent) the frame 11 from being separated downward from the user.

The cushion 19 may be disposed on a rear side of the frame 11, to reduce an impact applied to a user from the frame 11 while the pusher 14 is pushing the ground.

Figure 5:
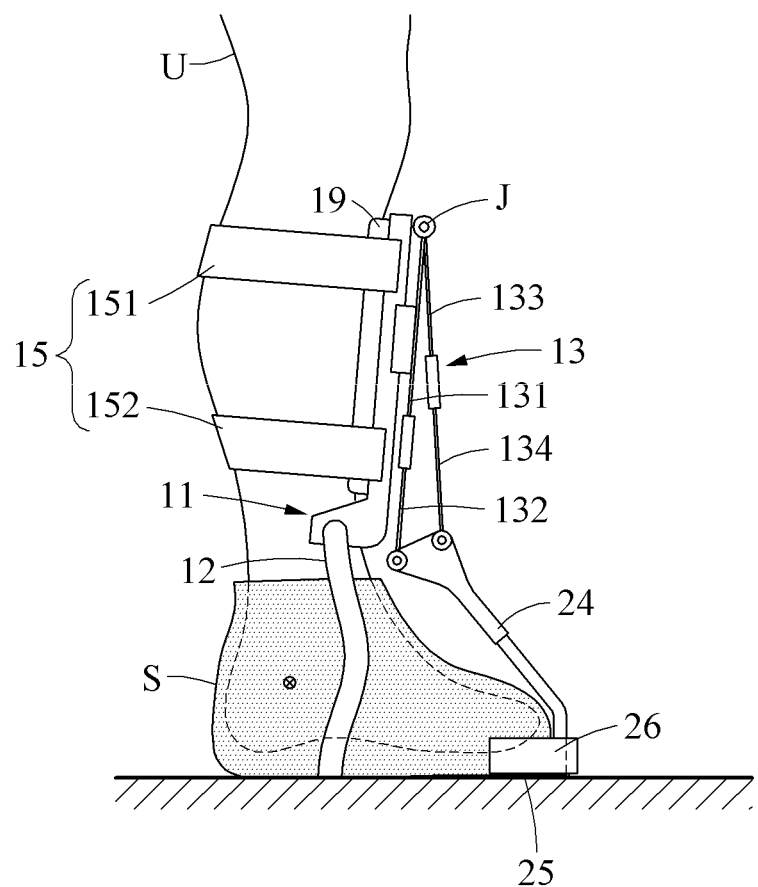
FIG. 5 is a side view illustrating another example of a walking assistance apparatus according to at least one example embodiment.
Figure 6:
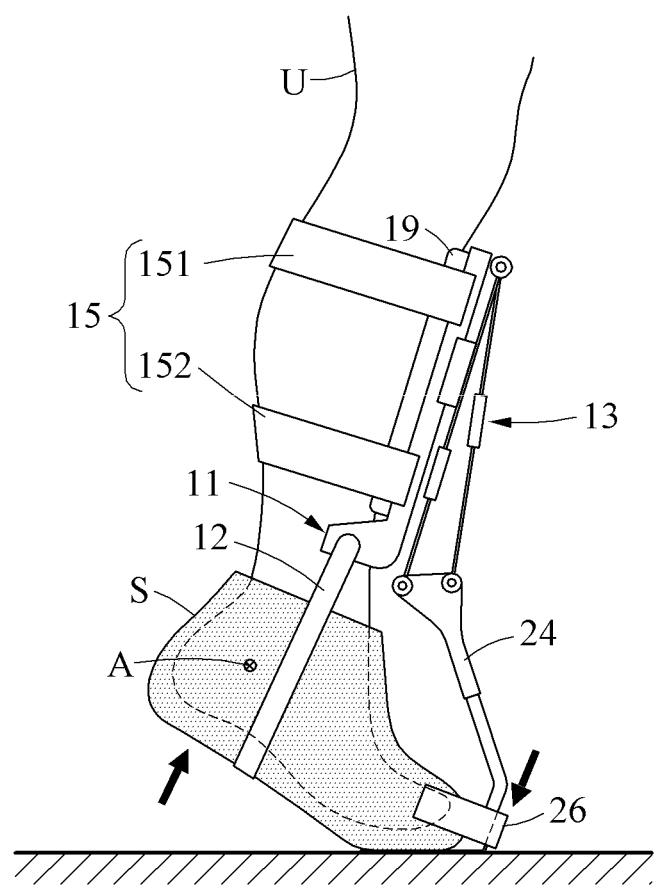
FIG. 6 illustrates another example in which a walking assistance apparatus according to at least one example embodiment assists a push-off motion.
Figure 8:
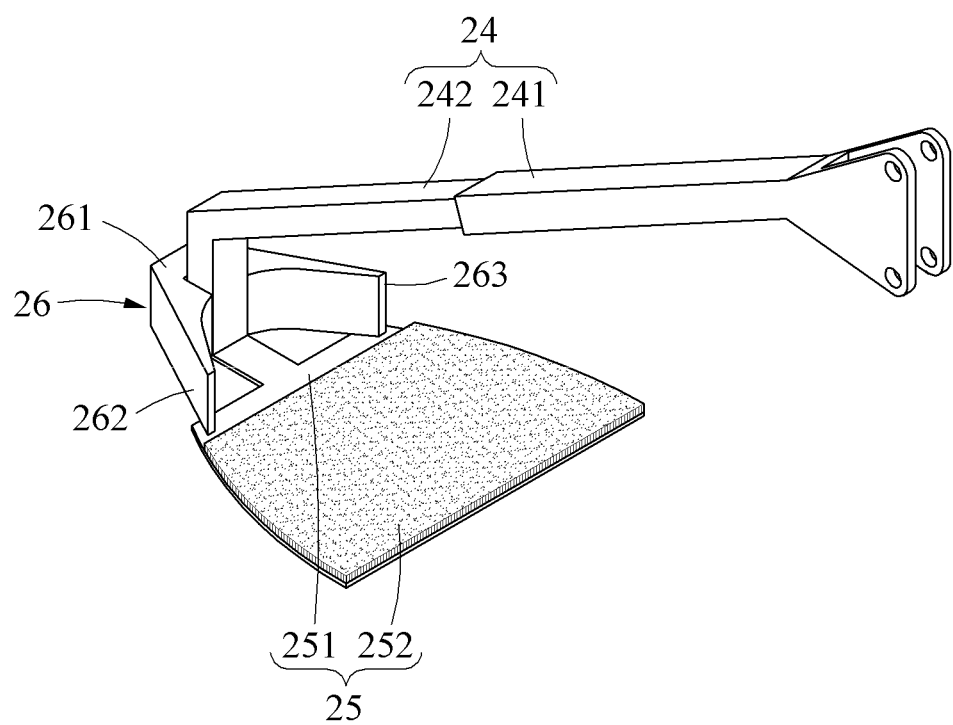
FIG. 8 is a perspective view illustrating a pusher according to at least one example embodiment.

FIG. 5 is a side view illustrating another example of a walking assistance apparatus according to at least one example embodiment, and FIG. 6 illustrates another example in which a walking assistance apparatus according to at least one example embodiment assists a push-off motion. FIG. 7 illustrates an example in which a walking assistance apparatus according to at least one example embodiment supports toes in a swing phase, and FIG. 8 is a perspective view illustrating a pusher according to at least one example embodiment.

Referring to FIGS. 5 through 8, a walking assistance apparatus 2 may include a pusher 24, a toe support 25, a cover 26, in addition to the frame 11, the sole support 12, the actuator 13, the wearable band 15, the cushion 19.

The pusher 24 may have an adjustable length. For example, the pusher 24 may include a first sub-pusher 241 and a second sub-pusher 242. The first sub-pusher 241 may be connected to the first rod 132 and the second rod 134 and may operate. The second sub-pusher 242 may slide along an inner wall and/or an outer wall of the first sub-pusher 241. A user may adjust the length of the pusher 24 by adjusting a relative location of the second sub-pusher 242 with respect to the first sub-pusher 241. The length of the pusher 24 may be adjusted based on a length of a foot of the user.

The toe support 25 may be connected to the pusher 24 and extend backward towards the foot of the user from the pusher 24, to support toes of the user. The toe support 25 may support the toes that are in a swing phase, to inhibit (or, alternatively, prevent) the user from falling. For example, the toe support 25 may be more flexible than the pusher 24. The toe support 25 may be deformed during a push-off operation of the user, and accordingly wearability of the user may be enhanced. The toe support 25 may include a support body 251 and an anti-slip member 252.

The support body 251 may be connected to the pusher 24 and extend backward towards the foot of the user. In an example, the support body 251 may have a shape of a flexible plate. In another example, the support body 251 may have a plurality of prongs.

The anti-slip member 252 may be disposed on the support body 251, to assist a foot (shoe) of the user to inhibit (or, alternatively, prevent) the foot from slipping on the support body 251. The anti-slip member 252 may include a material with a high coefficient of friction. The anti-slip member 252 may be, for example, a hook-and-loop fastener or a double-sided tape.

The cover 26 may be connected to the pusher 24 and extend backward from the pusher 24 towards the foot of the user, to cover a portion of a side of the foot. The cover 26 may include a cover body 261 that is connected to the pusher 24, a first cover extension portion 262 that extends backward and sideward from the cover body 261, and a second cover that extends portion 263 extending backward and sideward from the cover body 261 and that faces the first cover extension portion 262. For example, when the walking assistance apparatus 2 is worn on a right leg of the user, the first cover extension portion 262 may cover a side of a big toe of the user and the second cover extension portion 263 may cover a side of a little toe of the user.

Figure 9:
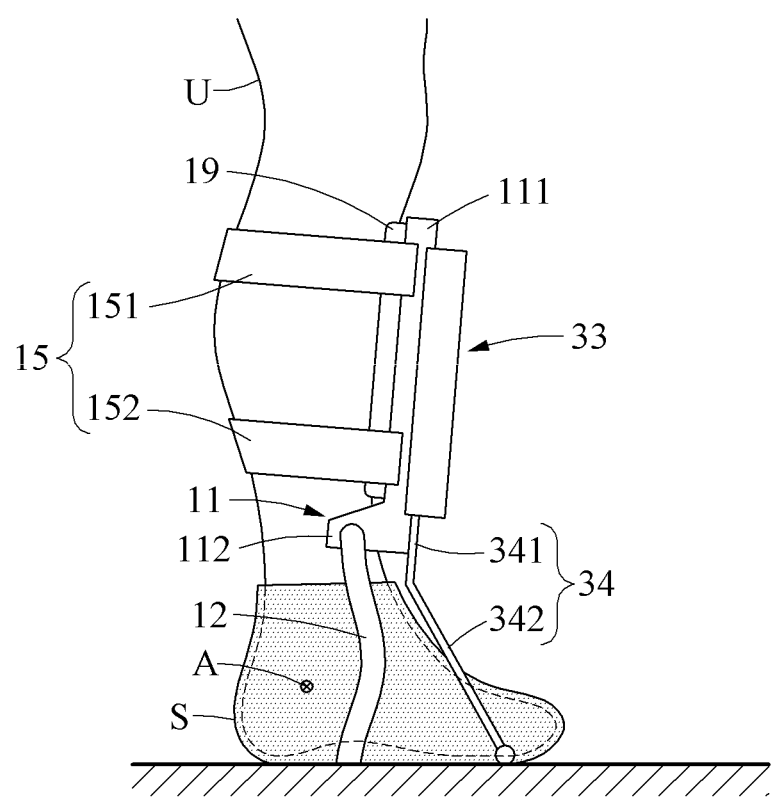
FIG. 9 is a side view illustrating another example of a walking assistance apparatus according to at least one example embodiment.
Figure 10:
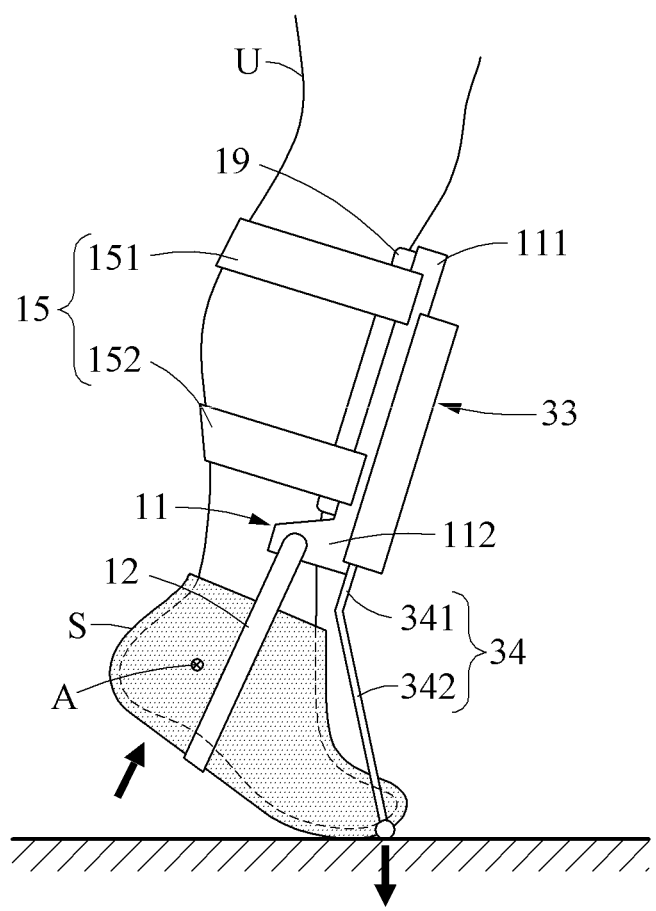
FIG. 10 illustrates another example in which a walking assistance apparatus according to at least one example embodiment assists a push-off motion.

FIG. 9 is a side view illustrating another example of a walking assistance apparatus according to at least one example embodiment, and FIG. 10 illustrates another example in which a walking assistance apparatus according to at least one example embodiment assists a push-off motion.

Referring to FIGS. 9 and 10, a walking assistance apparatus 3 may include an actuator 33 and a pusher 34, in addition to the frame 11, the sole support 12, the wearable band 15, and the cushion 19.

The actuator 33 may be a linear actuator. The actuator 33 may be mounted on the frame 11. The actuator 33 may allow the pusher 34 to perform a translation.

The pusher 34 may receive a power from the actuator 33 to perform a translation in one DOF. For example, the pusher 34 may receive a force for moving downward from the actuator 33, to push the ground. The pusher 34 may include a first pusher part 341 and a second pusher part 342.

The first pusher part 341 may be directly connected to the actuator 33 and may perform a reciprocating translation.

The second pusher part 342 may be bent forward from the first pusher part 341 and may be in contact with the ground. Referring to FIG. 9, when a user starts a push-off motion, the second pusher part 342 may be bent forward from the first pusher part 341, and thus the second pusher part 342 may be in contact with the ground in front of the first pusher part 341. For example, the second pusher part 342 may be in contact with the ground around toes of the user that are being in contact with the ground during a push-off motion of the user. In the above configuration, the pusher 34 may sufficiently lift the sole support 12 despite a small displacement.

Figure 11:
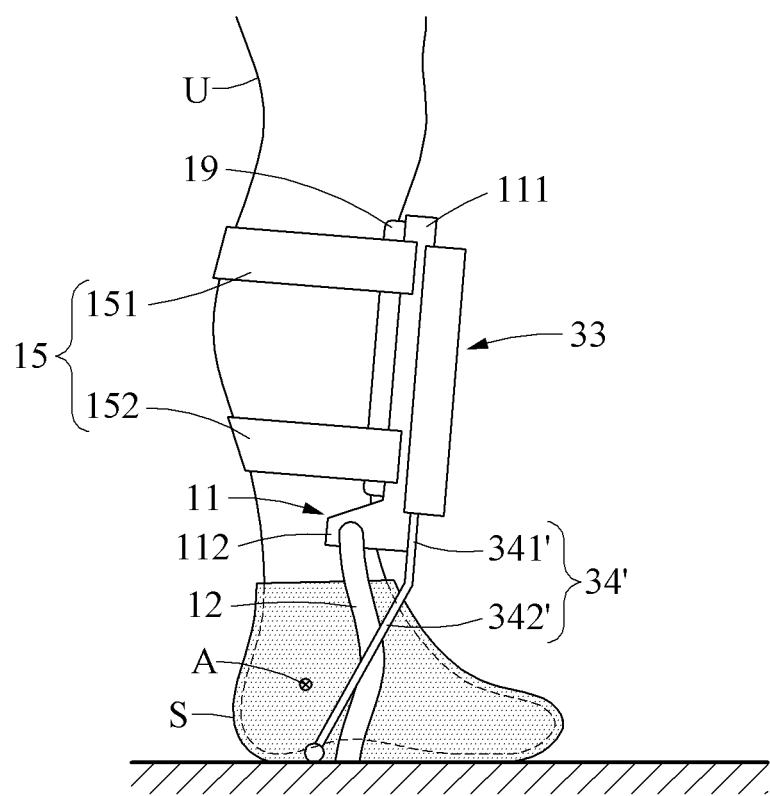
FIG. 11 is a side view illustrating another example of a walking assistance apparatus according to at least one example embodiment.
Figure 12:
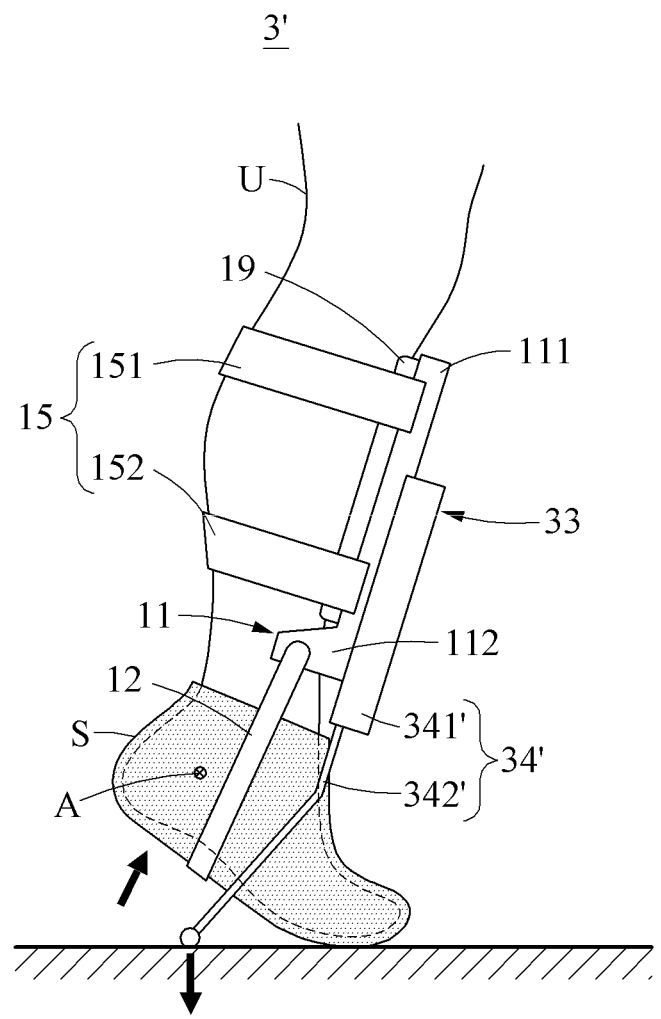
FIG. 12 illustrates another example in which a walking assistance apparatus according to at least one example embodiment assists a push-off motion.

FIG. 11 is a side view illustrating another example of a walking assistance apparatus according to at least one example embodiment, and FIG. 12 illustrates another example in which a walking assistance apparatus according to at least one example embodiment assists a push-off motion.

Referring to FIGS. 11 and 12, a walking assistance apparatus 3' may include an actuator 33 and a pusher 34', in addition to the frame 11, the sole support 12, the wearable band 15, and the cushion 19.

The pusher 34' may include a third pusher part 341' and a fourth pusher part 342'.

The third pusher part 341' may be directly connected to the actuator 33 and may perform a reciprocating translation.

The fourth pusher part 342' may be bent backward from the third pusher part 341' and may be in contact with the ground. In this example, a direction in which an assisting force acts may maximally coincide with a direction of a shin through a center of an ankle, and thus a push-off operation of a user may be effectively assisted using an actuator having a small output.

Figure 13:
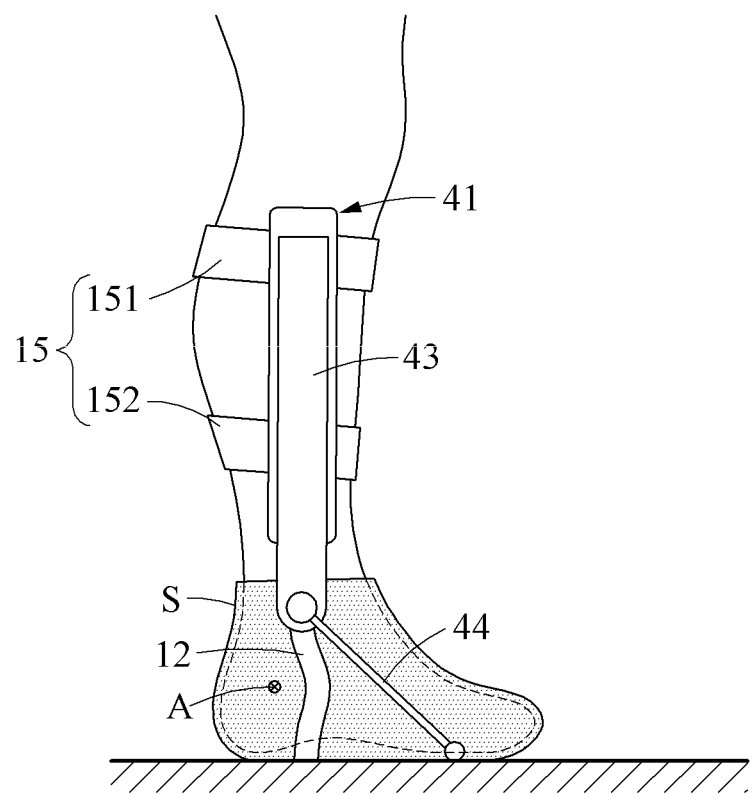
FIG. 13 is a side view illustrating another example of a walking assistance apparatus according to at least one example embodiment.
Figure 14:
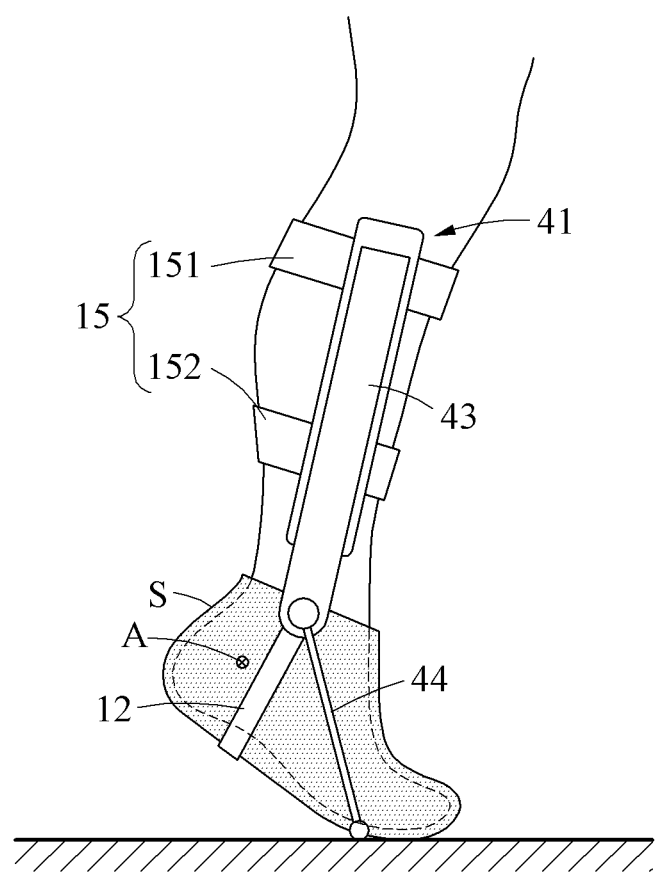
FIG. 14 illustrates another example in which a walking assistance apparatus according to at least one example embodiment assists a push-off motion.

FIG. 13 is a side view illustrating another example of a walking assistance apparatus according to at least one example embodiment, and FIG. 14 illustrates another example in which a walking assistance apparatus according to at least one example embodiment assists a push-off motion.

Referring to FIGS. 13 and 14, a walking assistance apparatus 4 may include a frame 41 an actuator 43, and a pusher 44, in addition to the sole support 12, the plurality of wearable bands 15, and the cushion 19.

The frame 41 may be disposed on a side of a lower leg of a user, however, example embodiments are not limited thereto. For example, the frame 41 may be disposed on a shin of the user.

The actuator 43 may generate a rotational power. For example, the actuator 43 may be a motor, and the like.

The pusher 44 may receive a power from the actuator 43 to perform a rotation in one DOF. For example, the pusher 44 may push the ground while rotating in a clockwise direction by the actuator 43. When the pusher 44 pushes the ground, the sole support 12 may lift a heel of a user.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A walking assistance apparatus comprising:
a frame configured to mount on a lower leg of a user;
a sole support connected to the frame, the sole support configured to support a sole of a foot of the user;
an actuator on the frame, the actuator configured to transfer power; and
a pusher indirectly connected to the sole support via the actuator and the frame and is not directly connected to the sole support, the pusher including a rigid member extending downward from the actuator towards a ground to transmit, based on the power applied from the actuator to the pusher, a force to push against the ground to assist plantar flexion motion of the foot of the user, and wherein the actuator includes,
a first rod movable with respect to the frame, the first rod configured to support a first portion of the pusher; and
a second rod movable with respect to the frame at a higher speed than that of the first rod, the second rod configured to support a second portion of the pusher.

2. The walking assistance apparatus of claim 1, wherein the sole support is configured to lift the sole of the foot while the pusher is pushing the ground.

3. The walking assistance apparatus of claim 1, wherein the pusher is configured to be spaced apart from the foot.

4. The walking assistance apparatus of claim 1, wherein
the first rod is configured to perform a translational motion with respect to the frame, and
the second rod is configured to perform the translational motion and a rotational motion with respect to the frame.

5. The walking assistance apparatus of claim 1, further comprising:
a toe support connected to the pusher such that the toe support extends towards the foot of the user from the pusher when the user wears the walking assistance apparatus, the toe support configured to support a toe of the user.

6. The walking assistance apparatus of claim 5, wherein a material of the toe support is more flexible than a material of the pusher.

7. The walking assistance apparatus of claim 6, further comprising:
a cover connected to the pusher such that the cover extends towards the foot of the user from the pusher when the user wears the walking assistance apparatus, the cover configured to cover a portion of a side of the foot of the user.

8. The walking assistance apparatus of claim 1, wherein the pusher is configured to perform a translational motion in one degree of freedom (DOF) with respect to the frame.

9. The walking assistance apparatus of claim 8, wherein the pusher comprises:
a first pusher part connected to the actuator, the first pusher part configured to receive the power from the actuator; and
a second pusher part connected to the first pusher part at an angle with respect to the first pusher part, the second pusher part configured to contact the ground when the user wears the walking assistance apparatus.

10. The walking assistance apparatus of claim 1, wherein the pusher is configured to perform a rotational motion in one DOF with respect to the frame.

11. The walking assistance apparatus of claim 1, wherein the sole support includes a first end and a second end, the first end and the second end each being connected to the frame such that the sole support is configured to enclose a heel of the user when the user wears the walking assistance apparatus.

12. The walking assistance apparatus of claim 1, wherein a length of the pusher is adjustable.

13. The walking assistance apparatus of claim 1, wherein the frame comprises:
a frame body configured to mount on the lower leg; and
a frame extension portion extending from the frame body towards the user to cover at least a portion of the lower leg of the user, the frame extension portion configured to support the sole support.

14. The walking assistance apparatus of claim 1, wherein the pusher has a end configured to at least indirectly push against the ground based on the power.

15. The walking assistance apparatus of claim 14, wherein the end of the pusher is not secured to the sole support such that the pusher is not directly connected to the sole support.

* * * * *